United States Patent [19]

Leonard et al.

[11] Patent Number: 5,296,711
[45] Date of Patent: Mar. 22, 1994

[54] TECHNIQUE FOR THE REMOTE DETECTION OF SEA SLICKS

[75] Inventors: Donald A. Leonard, Cupertino; Harold E. Sweeney, Menlo Park, both of Calif.

[73] Assignee: Atlantic Richfield Company, Los Angeles, Calif.

[21] Appl. No.: 971,872

[22] Filed: Nov. 5, 1992

[51] Int. Cl.$^5$ ............................................ G01N 21/65
[52] U.S. Cl. ................................. 250/372; 250/253; 250/301; 356/301
[58] Field of Search ............... 250/253, 372, 458.1, 250/459.1, 461.1, 301; 356/301

[56] References Cited

U.S. PATENT DOCUMENTS

| | | | |
|---|---|---|---|
| 3,745,566 | 7/1973 | Johnson | 250/301 X |
| 3,783,284 | 1/1974 | McCormack | 250/301 X |
| 3,899,213 | 8/1975 | Fantasia et al. | 250/301 |
| 4,081,215 | 3/1978 | Penney et al. | 356/301 X |
| 4,123,160 | 10/1978 | Caputo et al. | 356/301 |
| 4,945,249 | 7/1991 | Grant et al. | |

OTHER PUBLICATIONS

Sato et al., "Laser Radar for Remote Detection of Oil Spills", Applied Optics, vol. 17, No. 23, Dec. 1978, pp. 3798-3803.
H. Visser, "Teledetection of the thickness of oil films on polluted water based on the oil fluoescense properties", p. 1746, Applied Optics, vol. 18, No. 11.
H, Hoge, R. N. Swift, "Oil film thickness meausrement using airbourne laser-induced water Raman backscatter", pp. 3269-3281, Applied Optics, vol. 19, No. 19.

Primary Examiner—Constantine Hannaher
Assistant Examiner—Edward J. Glick
Attorney, Agent, or Firm—Joseph E. Rogers

[57] ABSTRACT

A method and apparatus for remote detection of an oil slick at or near the surface of the water using a combination of two or more ultraviolet lasers and comparing the relative magnitude of the received Raman backscattering signal magnitudes to determine the existence of the oil slick. The use of two different laser frequencies provides for elimination of atmospheric transmission variations and wave modulation.

17 Claims, 2 Drawing Sheets

TECHNIQUE FOR THE REMOTE DETECTION OF SEA SLICKS

FIELD OF THE INVENTION

This invention relates to the detection of oil slicks on the surface of water and more particularly to the use of differential absorption of Raman scattered light for such detection.

BACKGROUND OF THE INVENTION

To detect the presence of an oil film on the sea surface by means of a laser probe beam, two basic techniques have been demonstrated. These techniques are (1) the measurement of fluorescence emission from an oil film that has been excited by a probe beam, and (2) the measurement of the absorption by an oil film of the Raman backscatter from the bulk ocean water that has been excited by a probe beam.

There is a close wavelength similarity between the fluorescence spectrum of naturally occurring seawater substances, known as Gelbstoff, and the fluorescence spectrum of oil. This means that the fluorescence spectral signature, by itself, in many cases is not a good means of detecting thin oil films with a high degree of sensitivity. Therefore, a second independent physical measurement is needed. One such measurement technique is the Raman depression technique.

In the Raman depression technique, a pulsed laser beam is directed at the ocean surface. The beam that penetrates into the water interacts with the bulk water and produces Raman backscattering at a shifted wavelength. The difference between the wavelength of the pulsed laser beam and wavelength of light produced by Raman backscattering (Raman wavelength) is called the Raman shift. The magnitude of the return signal at the Raman wavelength is monitored with a receiver sensitive to the Raman wavelength. With uniform water properties, this magnitude is consistent from pulse to pulse. With an oil film on the surface and with the suitably chosen wavelength, for example, in the ultraviolet wavelength range where the absorption coefficient for oil is high, the magnitude of the return signal is noticeably reduced or depressed. This reduction in magnitude is used to detect the presence of the oil film.

The effect of an oil slick on the observed laser Raman backscatter signal that originates in a water column is given by equation (1)

$$S_r = S_r(o) \exp-(k_{ex}+k_r)D \qquad (1)$$

where $S_r$ = magnitude of observed Raman signal
$S_r(o)$ = magnitude of Raman signal without oil slick
$k_{ex}$ = l absorption coefficient at laser excitation wavelength
$k_r$ = absorption coefficient at Raman wavelength
$D$ = oil slick thickness Using the methods of the prior art, the difference in magnitude from one surface location to another would indicate the presence of oil on the surface.

Other effects, in addition to the absorption of Raman backscattered light in the oil film being detected, may also cause a decrease in the magnitude of the returned signal and thus introduce system noise. Examples of such effects are atmospheric transmission variations due to clouds, fog patches and haze layers, surface waves and subsurface variations in water attenuation. All of these effects can introduce modulations in the magnitude, indistinguishable from the absorption of the Raman wavelength in the oil film. Thus, these modulations constitute system noise.

Of the above system noise sources, the magnitude modulating action of surface waves is especially important since waves are nearly always present with amplitudes that will result in refractive effects that generate the type of system noise described in the preceding paragraph. This magnitude modulation is a result of the variable curvature of the air/water interface which acts as a dynamic optical lens. Surface waves thereby significantly limit the detectability of surface oil films.

The previous Raman depression technique requires a reference measurement without the oil film at a different time and at a different surface location. This means that measurements include system noise, such as that due to the wave modulation. Since these measurements are independent, the system noise can not be nulled. This limits the minimum detectable film thickness capability of the Raman depression technique.

Thus, there exists a need for a method detecting surface films that does not require independent measurements at two different locations to confirm the presence of an oil slick thereby nulling the effects of system noise.

SUMMARY OF THE INVENTION

Applicants method and apparatus for remote detection of an oil slick at or near a water surface include:

(a) directing a first and a second laser beams of different wavelength at substantially the same point on the water surface;

(b) receiving Raman shifted third and fourth light signals emanating from the water surface;

(c) measuring the magnitude the third and fourth light signals; and (d) ratioing the magnitudes of the third and fourth signals whereby the existence of a ratio other than one indicates the existence of oil on the water surface.

Applicant's invention not only solves the problems inherent in the prior art but also has several advantages including but not limited to minimizing the effects of wave modulation and other noise on the detection of oil on a water surface and dramatically decreasing the minimum detectable thickness of the oil slick.

BRIEF DESCRIPTION OF THE DRAWINGS

Features of the present invention will become apparent when reference is made to the following description taken in conjunction with the accompanying drawings in which.

DESCRIPTION OF THE PREFERRED EMBODIMENTS

Figure 1:
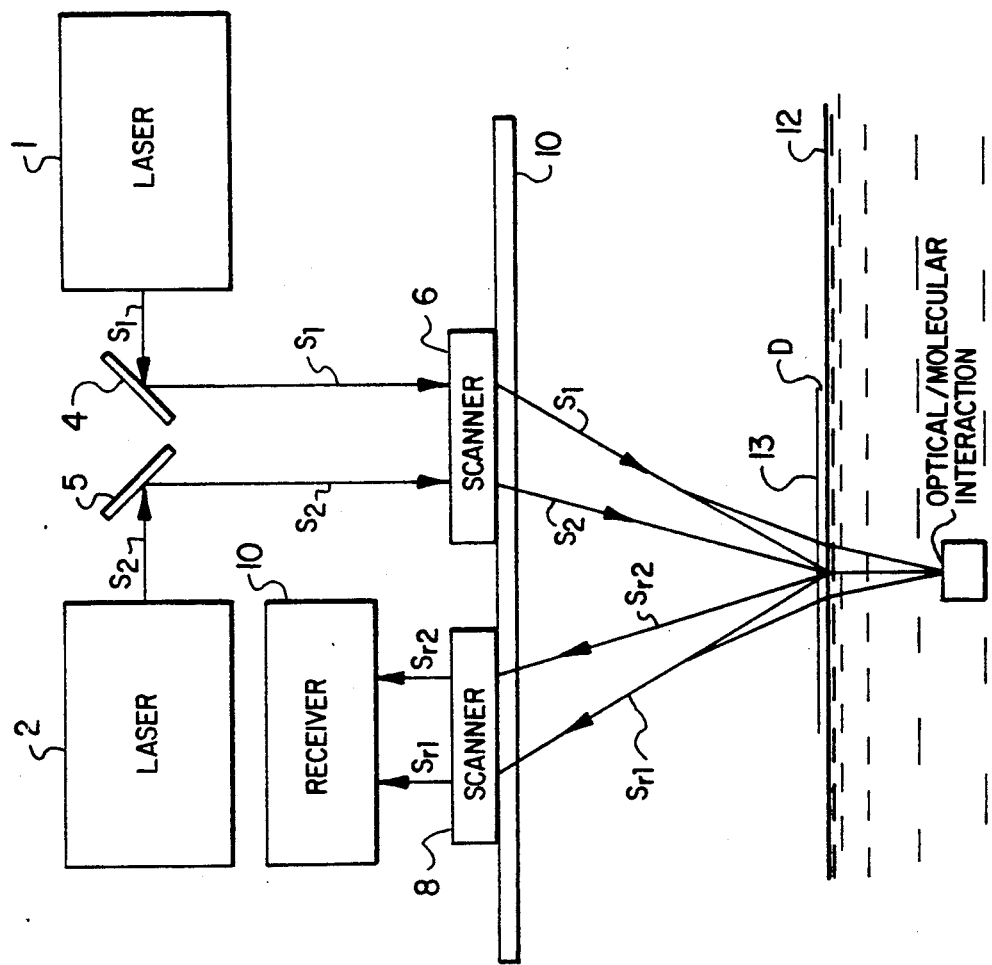
FIG. 1 is a diagrammatic representation of an airborne remote sensing system.

Referring to FIG. 1, there is shown a diagrammatic representation of an airborne remote sensing system. The system may be fitted within the interior of fuselage 10 of an aircraft and it includes an excimer laser 1 operating at a first primary ultraviolet radiation wavelength and emitting a pulsed beam $S_2$ of which is reflected by mirror 4 to transmit scanner 6. The system also includes a second excimer laser 2 operating at second primary ultraviolet radiation wavelength and emitting a pulsed beam $S_2$ of which is reflected by mirror 5 to transmit scanner 6. For example, laser 1 may be at a wavelength of 308 nm and laser 2 at a wavelength of 351 nm.

The pulse duration for pulsed primary beams $S_1$ and $S_2$ corresponding to lasers 1 and 2 respectively may be chosen to be between 25 and 40 nanoseconds. Such lasers are well known in the art and may be, for example, Questek Model 2580v beta, Lambda Physik Model LPX 240i or Lumonix Model Excimer 600. While two lasers are shown in FIG. 1, additional accuracy may be obtained by the use of additional lasers in a similar fashion.

Transmit scanner 6, which may be a mirror, directs and moves the location of incidence of beams $S_1$ and $S_2$ on the surface of the water 12. The beams $S_1$ and $S_2$ pass through any surface film 13 which may exist, are attenuated by an amount proportional to the product of the extinction coefficient $k_{ex}$ and film 13 thickness D. Upon entering the water 12, the beams each interact with the water molecules producing omni-directional Raman scattering. The backscattering signals $S_{r1}$ and $S_{r2}$ emerge from the surface and are each attenuated by $k_rD$. $S_{r1}$ and $S_{r2}$ are received through receive scanner 8 which scans water surface in a coordinated fashion with transmit scanner 6. $S_{r1}$ and $S_{r2}$ are thereby directed to receiver 10. Scanners 8 and 6 operate cooperatively. Receiver 10 will have a spectral response capable of receiving the signals $S_{r1}$ and $S_{r2}$ and be capable of gating on and off in less than 10 nanoseconds as well as having a gain of approximately $10^4$. Such detectors are available such as, multi-anode MCPPMT, e.g. Hammamatsu 4110.

Figure 2A:
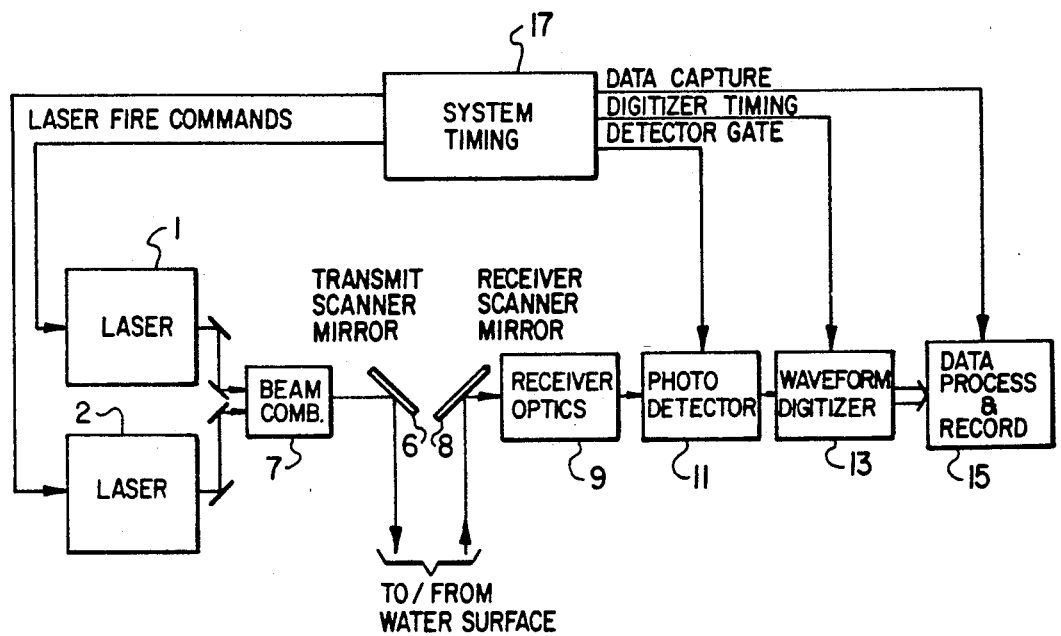
FIG. 2A is a block diagram of a typical remote sensing system.

FIG. 2A is a simplified block diagram of a typical remote sensing system. The beams from lasers 1 and 2 are combined and directed through beam combiner 7 to the transmit scanner 6 and thereby to a position on the water surface 12. Receiver scanner 8 position is coordinated with that transmit scanner 6 and directs the backscattered radiation from the identical surface position into the receiver optics 9 where it is filtered and focused onto the photo detector 11 in the focal plane. Photo detector 11, which may be e.g. a Hammamatsu R4110or other similar detector, converts the light intensity into a voltage waveform and is in electronic communication with waveform digitizer 13. Waveform digitizer 13 which may be e.g. an ANALYTEK series 2000 digitizer or other similar wave form digitizer, digitizes the voltage waveform output of photo detector 11. The waveform digitizer 13 is in electronic communication with the data processor. Waveform digitizer 13 provides digital words corresponding to the digitized waveform to the data processor 15 for analysis and storage. The analysis algorithm is described below.

Figure 2B:
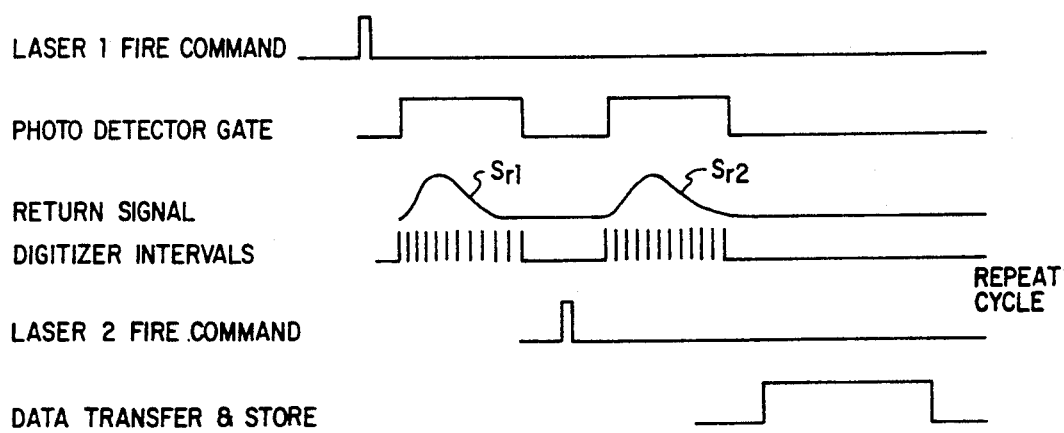
FIG. 2B is a simplified timing diagram for a system similar to that shown in FIG. 2A.

FIG. 2B is a simplified timing sequence for a system similar to that shown in FIG. 2A. Laser 1 is commanded to fire a pulse at wavelength $\lambda_1$ by system timing 17. After an appropriate delay to account for the time of flight of the pulse to water surface 12 and back, photo detector 11 has gate or "shutter" (not shown) which is opened on command by the system timing 17 and the Raman signal corresponding to $\lambda_1$, $\lambda_{r1}$, is received. As this signal is received, the waveform digitizer 13 provides a set of voltage levels at a sequence of time intervals corresponding to returns from sequential depths.

After receipt of $\lambda_{r1}$ signal is completed, laser 2 is immediately commanded to fire by system timing 17. At the appropriate time the photo detector 11 gate is again commanded open by system timing 17 and the $\lambda_{r2}$ signal is received and digitized in like manner.

The digitized data is transferred into the data processor 15 for processing according to the appropriate algorithm described below.

A complete system might also include navigational aids and scanner pointing data to identify the location being interrogated and this location data is stored with the signal received (not shown). Operator displays monitoring the equipment status as well as a "quick look" at sampled processed data during the mission (not shown) may also be included to provide real time operator interaction if desired.

A general and well known property of oils is that their absorption coefficient in the ultraviolet range increases sharply as the probing wavelength decreases. This property permits interrogation at a single surface location using beams S1 and S2 lasers at different ultraviolet wavelengths with two corresponding water Raman beams $S_{r1}$ and $S_{r2}$. The magnitudes of beams $S_{r1}$ and $S_{r2}$ will be markedly different because of the different oil film absorption at the different wavelengths of beams $S_{r1}$ and $S_{r2}$.

Because beams $S_1$ and $S_2$ are initiated simultaneously, or near simultaneously, and directed at a common location on the water surface 12, the modulation of the magnitude of beams $S_{r1}$ and $S_{r2}$ induced by waves and other system noise will be highly correlated and will be cancelled when the two Raman return signals are ratioed.

If a ratio the two Raman signals beams $S_{r1}$ and $S_{r2}$ is used for normalization to remove noise, such a ratio is given by equation (2)

$$S_{r1}/S_{r2}=(S_{r1}(o)/S_{r2}(o))exp-[(k_{ex1}+k_{r1})- (k_{ex2}+k_{r2})]D \qquad (2)$$

$$S_{r1}/S_{r2}=(S_{r1}(o)/S_{r2}(o))exp -[\Delta k]D \qquad (3)$$

where $S_{r1}$ and $S_{r2}$ = the magnitude of two observed Raman signals $S_{r1}(o)$ and $S_{r2}(o)$ = the magnitude of two Raman signals with no oil present $k_{ex1}$ = extinction coefficient at the wavelength of $S_1$
$k_{ex2}$ = extinction coefficient at the wavelength of $S_2$
$k_{r1}$ = extinction coefficient at the wavelength of $S_{r1}$
$k_{r2}$ = extinction coefficient at the wavelength of $S_{r2}$
$\Delta k$ = differential absorption coefficient, defined as $[(k_{ex1}+k_{r1})-(k_{ex2}+k_{r2})]$.

In general, the larger the value of $\Delta k$, the more sensitive the measurement can be, i.e., the minimum detectable oil thickness is less for a given system signal-to-noise ratio (SNR). The signal-to-noise ratio can calculated by rewriting equation (3) as follows:

$$z=S_{r1}/S_{r2}=(S_{r1}(o)/S_{r2}(o))exp-(\Delta k\ D) \qquad (4)$$

Differentiating with respect to D $$dz/z=-\Delta k\ d(D) \qquad (5)$$

Identifying dz/z as the noise to signal ratio $(SNR)^{-1}$ and d(D) as the minimum detectable thickness D(min), therefore $$D(min)=1/(\Delta k\ SNR) \qquad (6)$$

The SNR of the ratio of beams $S_{r1}$ and $S_{r2}$ that is necessary to achieve the required minimum detectable thickness can now be calculated from equation (6).

An example which illustrates this calculation is the use of excimer lasers at wavelengths of 308 nm and 351 nm for beams $S_1$ and $S_2$ would produce beams $S_{r1}$ and $S_{r2}$ at wavelengths of 344 nm and 398 nm respectively. The absorption coefficient for oil is a monotonic function of wavelength from 300 to 450 nm, becoming increasingly more absorbing as the wavelength becomes shorter. The value of k used in this analysis are those for weakly absorbing oil taken from H. Visser, Appl. Opt. 18, 1746 (1979). In the region from 300–450 nm an empirical curve with the equation $k=2290(\lambda/100)^{-7.5}$ fits Visser's data where $\lambda$ is the wavelength in nm and k is the absorption coefficient in $\mu m^1$. Based on this data the wavelengths and corresponding absorption coefficients for the dual excimer example are:

| Wavelength | Absorption Coefficient |
|---|---|
| 308 nm | 0.496 $\mu m^{-1}$ |
| 344 | 0.217 |
| 351 | 0.186 |
| 398 | 0.073 |

With these values the differential absorption coefficient $\Delta k = 0.496 + 0.217 - (0.186 + 0.073) = 0.454$. Using equation (6) this means that $D_{min} = 0.01$ $\mu m$ could be obtained with a SNR=220.

In the ultraviolet region of the spectrum, typical sea water exhibits a difference in the diffuse attenuation coefficient as a function of wavelength. This leads to differences in the effective depth of the Raman backscatter as shown in FIG. 3.

Figure 3:
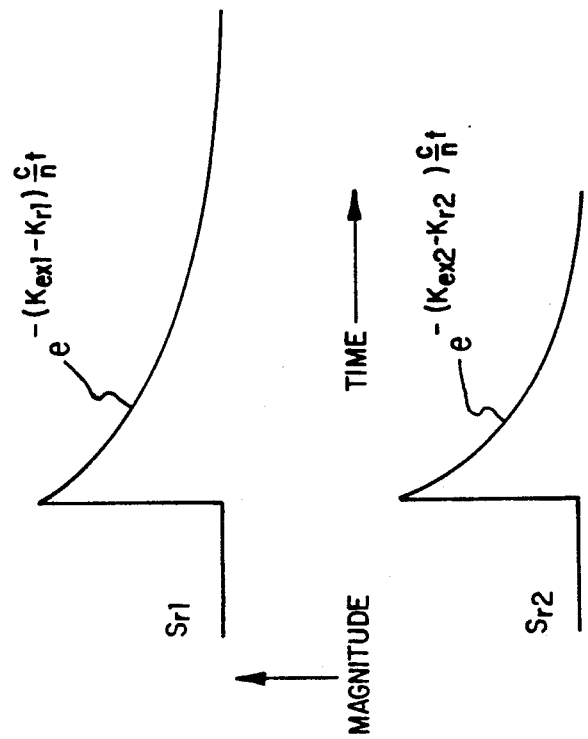
FIG. 3 is a graphical representation of the concept of effective depth.

FIG. 3 is a graphical representation of the concept of effective depth. FIG. 3 shows two curves which relate to the effect that different incident frequencies have on effective depth. In the absence of a surface film, the return signals at the two Raman wavelengths will be attenuated at different rates because the instantaneous signal level is proportional to the range or depth in the scatterer. Scattering at a greater depth will produce a weaker signal because of the greater accumulated attenuation.

As a consequence of the difference between the diffuse attenuation or extinction coefficients of the water, $K_s$, the rate of attenuation is different. If the total return signals ($S_{r1}$ or $S_{r2}$) are accepted and integrated, the magnitudes will be proportional to the effective depths which are seen to be dissimilar as defined by the following equations where Effective time of return signals ($t_{eff}$) are:

$$S_{r1}: t_{eff1} = (n/c)(K_{ex1} + K_{r1})$$

$$S_{r2}: t_{eff2} = (n/c)(K_{ex2} + K_{r2})$$

and Effective Depth $(d_{eff}) = t_{eff} \times c/n$ $$S_{r1}: d_{eff1} = 1/(K_{ex1} + K_{r1})$$

$$S_{r2}: d_{eff2} = 1/(K_{ex2} + K_{r2})$$

n: index of refraction of water; and
c: speed of light

Therefore, the magnitudes of the integrated return signals as can be seen in FIG. 3 are not matched in the absence of a surface film and are dependent on the water properties. This mismatch in magnitudes caused by the difference in effective depth can easily be overcome by accepting only the initial portions of the return signals (i.e. range gating).

The differences in effective depth caused by surface waves can be mathematically described by the following equation:

$$\theta/\theta \cdot = (1/n)(1/[1-(d_{eff}/R)(1-(1/n))]) \tag{9}$$

where
$\theta$ = scattering angle in air
$\theta \cdot$ = scattering angle in water
n = index of refraction of water
$d_{eff}$ = effective depth at which the scattering occurs
R = radius of curvature of the water surface Therefore, the wave modulation of the two return signals will not perfectly cancel when the diffuse attenuation coefficient is different for the two wavelengths, because $d_{eff}$ will be different and the dependence on R is not the same for the two different wavelengths.

Range gating reduces the effects of surface contributions to system noise. The effect of differences in the observed effective depth of the two Raman backscatter signals can be reduced, thereby allowing a better correlation between the wave modulation effects on the two beams $S_{r1}$ and $S_{r2}$. This enables a better degree of cancellation when the magnitude of beams $S_{r1}$ and $S_{r2}$ are ratioed.

Wave noise has been observed to modulate the Raman signal by as much as 20% (peak-to-peak). By ratioing the Raman signals and range gating to decrease the effective depth effects the wave noise can be suppressed by over an order of magnitude making possible detection with SNR greater than 100.

Although several embodiments have been described in detail, it should be understood that various changes, substitutions and alterations can be made therein without departing from the spirit and scope of the invention as defined by the appended claims.

What is claimed is:

1. A method for remote detection of an oil slick at or near a water surface comprising:
    (a) directing a plurality of beams of different wavelengths at substantially the same point on the water surface;
    (b) receiving a plurality of Raman shifted signals emanating from the water surface which result from said step of directing a plurality of beams;
    (c) measuring the magnitude of each of the plurality of Raman shifted signals; and
    (d) ratioing the magnitudes of each of the plurality of Raman shifted signals whereby the existence of a ratio other than one indicates the existence of oil slick on the water surface.

2. The method of claim 1 wherein each of the beams in the plurality of beams in the ultraviolet frequency range.

3. The method of claim 2 wherein each of the beams in said plurality of beams has a wavelength which is sufficiently different from the wavelength of each of the other beams of said plurality of beams such that each of the Raman shifted signals of said plurality of Raman shifted signals is differentially absorbed in the oil slick.

4. The method of claim 3 wherein the wavelength of each of the beams of said plurality of beams is sufficiently different from the wavelength of each of the other beams of said plurality of beams such that a differential absorption coefficient for said plurality of Raman shifted signals is maximized.

5. The method of claim 1 wherein the step of receiving further comprises receiving each of said plurality of Raman shifted signals over a predetermined time window corresponding to an effective depth of an apparent point of generation of each of said plurality of Raman shifted signals.

6. A method for remote detection of an oil slick at or near a water surface comprising:
   (a) providing a plurality of beams of different wavelengths each of the plurality of beams having a wavelength in the ultraviolet frequency range which is sufficiently different from the wavelength of each of the other beams of said plurality of beams such that a differential absorption coefficient for resulting Raman shifted signals generated in the oil slick is maximized;
   (b) directing said plurality of beams of different wavelengths at substantially the same point on the water surface;
   (c) receiving a plurality of Raman shifted signals emanating from the water surface over a predetermined time window corresponding to an effective depth of the apparent point of generation of each of said plurality of Raman shifted signals resulting from said step of directing a plurality of beams;
   (d) measuring the magnitude of each of the plurality of Raman shifted signals; and
   (e) ratioing the magnitudes of each of the plurality of Raman shifted signals whereby the existence of a ratio other than one indicates the existence of an oil slick on the water surface.

7. A method for remote detection of an oil slick at or near a water surface comprising:
   (a) directing a first and a second laser beams of different wavelengths at substantially the same point on the water surface;
   (b) receiving a Raman shifted third and fourth light signal emanating from the water surface resulting from said step of directing said first and second laser beams;
   (c) measuring the magnitude of the Raman shifted third and fourth light signals; and
   (d) ratioing the magnitudes of the Raman shifted third and fourth light signals whereby the existence of a ratio other than one indicates the existence of an oil slick on the water surface.

8. The method of claim 7 wherein the wavelengths of said first and second laser beams are in the ultraviolet frequency range.

9. The method of claim 8 wherein said wavelengths are sufficiently different such that the Raman shifted third and fourth signals resulting from each of said first and second beams is differentially absorbed in the oil slick.

10. The method apparatus of claim 9 wherein said wavelengths are sufficiently different such that a differential absorption coefficient for the Raman shifted third and fourth signals in the oil slick is maximized.

11. The method of claim 7 wherein the step of receiving further comprises receiving said Raman shifted third and fourth light signals over a predetermined time window corresponding to an effective depth of an apparent point of generation of said Raman shifted third and fourth signals.

12. A method for remote detection of an oil slick at or near a water surface comprising:
   (a) providing a first and a second laser beam of different wavelengths each of the first and second laser beams having a wavelength in the ultraviolet frequency range which are sufficiently different from each other such that a differential absorption coefficient for resulting Raman shifted signals in the oil slick is maximized;
   (b) directing said first and second laser beams at substantially the same point on the water surface;
   (c) receiving Raman shifted third and fourth signals resulting from said step of directing emanating for the water surface over a predetermined time window corresponding to an effective depth of an apparent point to generation of each of said third and fourth Raman shifted signals;
   (d) measuring the magnitude of the Raman shifted third and fourth signals; and
   (e) ratioing the magnitudes of the third and fourth Raman shifted signals whereby the existence of a ratio other than the one indicates the existence of an oil slick on the water surface.

13. A laser apparatus for remotely detecting the presence of an oil slick on or near a water surface comprising:
   (a) a first laser generator for generating a first laser light beam at a first wavelength;
   (b) a second laser generator for generating a second laser light beam of a second wavelength;
   (c) a transmit scanner for directing said first and second laser light beams at substantially the same point on the water surface;
   (d) an optical receiver for receiving Raman shifted third and fourth light signals resulting from the interaction of said first and second laser light beams with the oil slick and the water and for ratioing the magnitudes of the third and fourth light signals whereby the existence of a ratio other than one indicates the existence of an oil slick on or near the water surface.

14. The apparatus of claim 13 wherein the first and second wavelengths are in the ultraviolet frequency range.

15. The apparatus of claim 13 wherein the first and second wavelengths are sufficiently different such that said Raman shifted third and fourth light signals are differentially absorbed in an oil slick.

16. The apparatus of claim 13 wherein the first and second wavelengths are sufficiently different such that a differential absorption coefficient for the Raman shifted third and fourth light signals in an oil slick is maximized.

17. The apparatus of claim 13 wherein the optical receiver includes a timing system for receiving Raman shifted third and fourth light signals over a predetermined time window corresponding to an effective depth of an apparent point of generation of said Raman shifted third and fourth light signals.

* * * * *